US00PP36456P2

(12) United States Plant Patent
Wilkoński

(10) Patent No.: US PP36,456 P2
(45) Date of Patent: Feb. 18, 2025

(54) ***SPIRAEA* PLANT NAMED 'Golden Jack'**

(50) Latin Name: *Spiraea japonica*
Varietal Denomination: Golden Jack

(71) Applicant: Karol Wilkoński, Skierniewice (PL)

(72) Inventor: Karol Wilkoński, Skierniewice (PL)

(73) Assignee: SZKÓLKA ROSLIN OZDOBNYCH WILKONSCY, Skierniewice (PL)

( * ) Notice: Subject to any disclaimer, the term of this patent is extended or adjusted under 35 U.S.C. 154(b) by 0 days.

(21) Appl. No.: 18/594,047

(22) Filed: Mar. 4, 2024

Related U.S. Application Data

(60) Provisional application No. 63/450,360, filed on Mar. 6, 2023.

(51) Int. Cl.
*A01H 5/02* (2018.01)
*A01H 6/74* (2018.01)

(52) U.S. Cl.
USPC ..... Plt./226

(58) Field of Classification Search
USPC ..... Plt./226
CPC ... A01H 5/02; A01H 5/12; A01H 5/00; A01H 6/74
See application file for complete search history.

(56) References Cited

PUBLICATIONS

Van Vliet Plants Catalog 2020 retrieved on Jul. 1, 2024 at https://newplants.nl/uploads/Catalogue-2020.pdf, 1-3 and 54-56. (Year: 2020).*

YouTube video Van Vliet New Plants 2021 retrieved on Jul. 1, 2024 at https://www.youtube.com/watch?v=gnWP0ygMUDU, one page. (Year: 2021).*

* cited by examiner

*Primary Examiner* — June Hwu
(74) *Attorney, Agent, or Firm* — Penny J. Aguirre

(57) ABSTRACT

A new cultivar of *Spiraea* plant named 'Golden Jack' that is characterized by its compact and spreading plant habit, its foliage with young leaves that are bright yellow in color and mature to green-yellow in color, its flowers that are purple-pink in color, and its floriferous blooming habit.

2 Drawing Sheets

Botanical classification: *Spiraea japonica.*
Variety denomination: 'Golden Jack'.

BACKGROUND OF THE INVENTION

The present invention relates to a new and distinct cultivar of *Spiraea japonica* referred to hereafter by its cultivar name, 'Golden Jack'. 'Golden Jack' is a new variety of *Spiraea* shrub grown for landscape use.

'Golden Jack' was discovered as a chance seedling in a production field in summer of 1999 in Skierniewice, Poland. The parents are unknown; however, the parents are believed to be *Spiraea japonica* cultivars 'Lisp' (U.S. Plant Pat. No. 7,537) and 'Goldmound' (not patented) based on the characteristics of the new cultivar and that the claimed plant was found next to plants of 'Lisp' and 'Goldmound' that were growing in the vicinity.

Asexual propagation of the new cultivar was first accomplished by the Inventor by softwood stem cuttings in August of 2000 in Skierniewice, Poland. Asexual propagation of the new cultivar by softwood stem cuttings has determined that the characteristics of the new cultivar are stable and are reproduced true to type in successive generations.

SUMMARY OF THE INVENTION

The following traits have been repeatedly observed and are determined to be the characteristics of the new cultivar. These attributes in combination distinguish 'Golden Jack' as a new and unique cultivar of *Spiraea.*

1. 'Golden Jack' exhibits a compact and spreading plant habit.
2. 'Golden Jack' exhibits foliage with young leaves that are bright yellow in color and mature to green-yellow in color.
3. 'Golden Jack' exhibits flowers that are purple-pink in color.
4. 'Golden Jack' exhibits a floriferous blooming habit.

Both the probable female and male parents 'Lisp' and 'Goldmound' differ from 'Golden Jack' in having a less compact and less spreading plant habits and leaves that are wider and larger in size, In addition, 'Goldmond' differs from 'Golden Jack' in having leaves that remain clear yellow throughout the season and in being more susceptibility to powdery mildew and leaf scorch. 'Golden Jack' can also be most closely compared to the *Spiraea* cultivars 'Goldflame' (not patented) and 'Davcop01' (U.S. Plant Patent No, 31,996). 'Goldflame' and 'Davcop01' are both similar to 'Golden Jack' in having foliage that is yellow in color in summer and flowers that are purple-pink in color. 'Goldflame' differs from 'Golden Jack' in having a much less compact plant habit, young foliage that is orange to orange-red in color, and flowers that are lighter purple-pink in color. 'Davcop01' differs from 'Golden Jack' in having a less compact and less spreading plant habit, young foliage that is orange to orange-red in color, and a less floriferous blooming habit.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include website listings by YouTube, Visions Pictures, Hoogenraad Plant, Leskovo-Pitomnik, Flora Planet, Parko, e-Katalogroslin, sklep ogrody Wloclawek, opt-hoz, shop gardenplants, Van Vliet New Plants, dekorsad56, Florarbo, Nurgapuukool, Gradinamax, Dolina-sad, Juragiumedelynas, Dolina-sad, and shop glendoick.

BRIEF DESCRIPTION OF THE DRAWINGS

The accompanying color photographs illustrate the overall appearance and distinct characteristics of the new *Spiraea*. The photographs were taken of a plant 2.5 years in age as grown outdoors in a trial garden in Stroe, The Netherlands.

The photograph in FIG. 1 provides a view of the overall plant habit of 'Golden Jack' in bloom.

Figure 1:
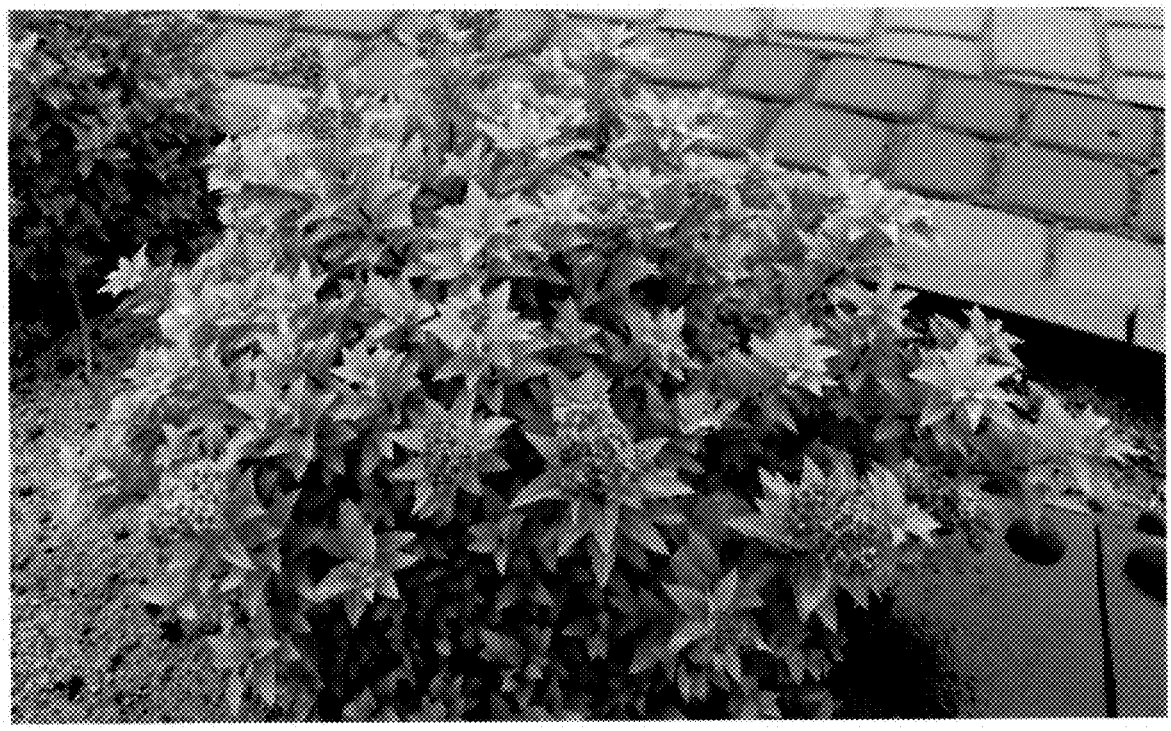
Figure 2:
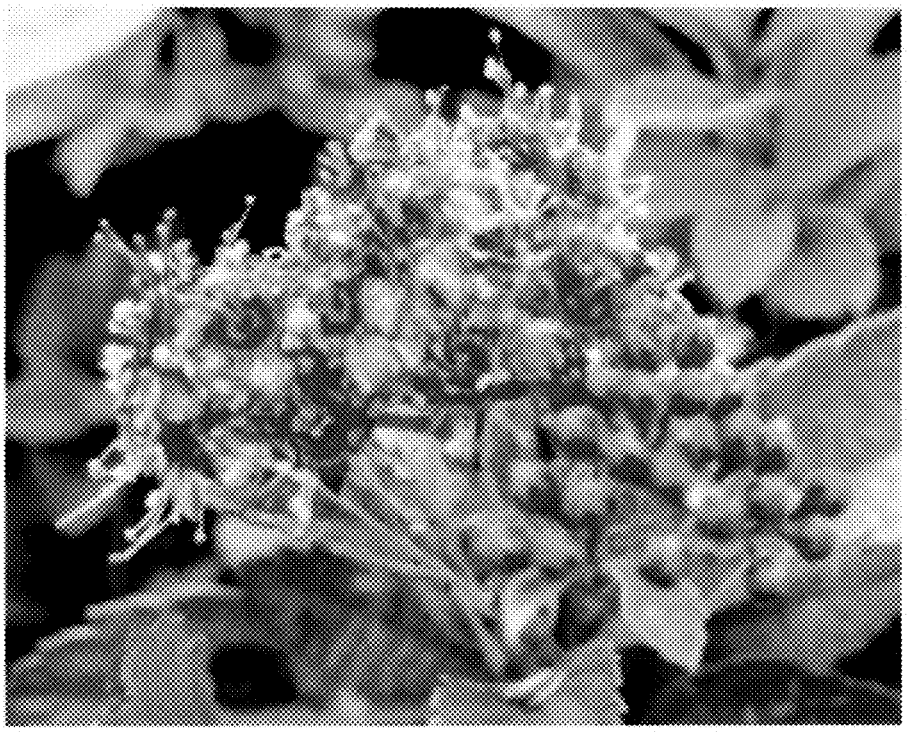

The photograph in FIG. 2 provides a close-up view an inflorescence of 'Golden Jack'.

Figure 3:
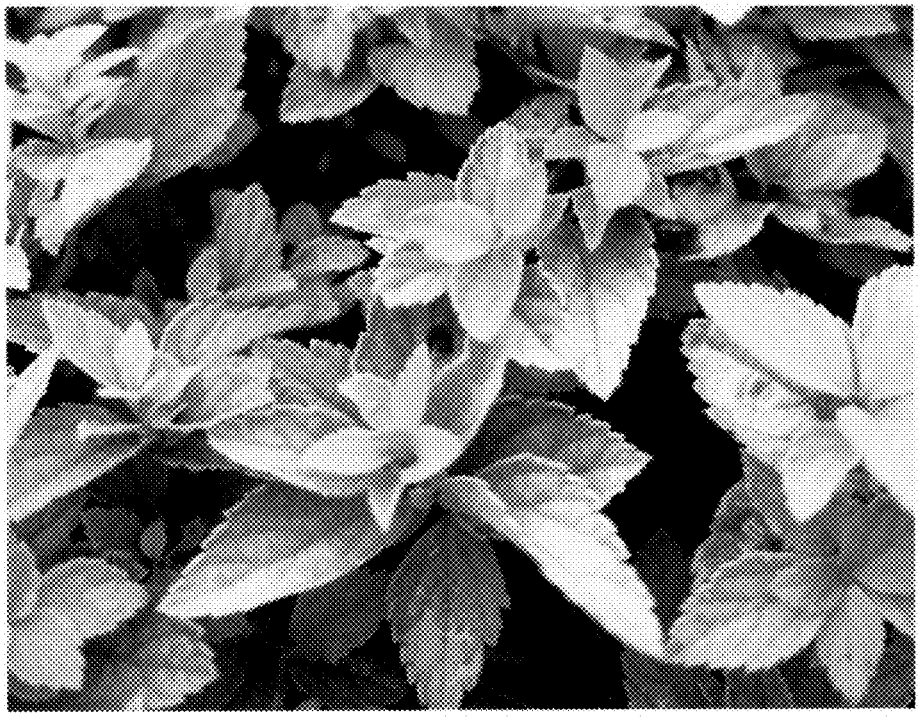

The photograph in FIG. 3 provides a view of the spring foliage of 'Golden Jack'.

The colors in the photographs are as close as possible with the photographic and printing technology utilized and the color values cited in the detailed botanical description accurately describe the colors of the new *Spiraea*.

DETAILED BOTANICAL DESCRIPTION

The following is a detailed description of plants 2.5 years in age as grown in a trial garden in Stroe, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—May to June in Poland.

*Plant type*.—Deciduous shrub.

*Plant habit*.—Compact, spreading.

*Height and spread*.—An average of 50 cm in height and 70 cm width.

*Hardiness*.—At least in U.S.D.A. Zones 4 to 8.

*Diseases and pests*.—Has shown low susceptibility to powdery mildew (typically caused by *Podosphaera spiraeae*) when grown in The Netherlands, no resistance or susceptibility has been shown to pests has been observed.

*Root description*.—Fibrous and fine.

*Propagation*.—Softwood stem cuttings.

*Growth rate*.—Moderate.

*Root development*.—8 to 10 weeks for root initiation, an average of 9 months to produce a young rooted plant from a rooted cutting.

Branch description:

*Branch shape*.—Rounded.

*Branch color*.—Young; 151A with tips 178B, mature; 154C, blotched with N199C, 200C, 200D, older branches and bark; a blend of N199C, N199D, and 200C.

*Branch size*.—Average of 23.1 cm in length, 2.5 mm in diameter.

*Branch strength*.—Strong.

*Branch surface*.—Young; slightly glossy, densely covered with soft adpressed pubescence, 0.5 mm in length, too small to measure color, mature and bark; matte.

*Internode length*.—An average of 1.2 cm.

*Branching*.—An average of 30 main stems, an average of 90 lateral branches per main plant, held in an average angle of 55° (varying between 20° and 90°).

Foliage description:

*Leaf shape*.—Ovate to broadly elliptic.

*Leaf division*.—Simple.

*Leaf base*.—Acute.

*Leaf aspect*.—Slightly carinate.

*Leaf apex*.—Acute to narrow acute.

*Leaf fragrance*.—None.

*Leaf venation*.—Pinnate, upper surface; a blend of 149A and 150A, lower surface a blend of 145A and 145B.

*Leaf margins*.—Serrated to biserrated.

*Leaf arrangement*.—Alternate.

*Leaf attachment*.—Petiolate.

*Leaf surface*.—Both surfaces slightly glossy and non-rugose, upper surface sparsely pubescent with very short soft hairs 0.3 mm in length, too small to measure color, lower surface moderately pubescent with very short soft hairs 0.3 mm in length, too small to measure color.

*Leaf size*.—Average of 3.6 cm in length and 1.9 cm in width.

*Leaf quantity*.—Average of 20 per lateral branch.

*Leaf color*.—Young upper surface; 9A and lightly suffused with 178B, young lower surface; 13B to 13C, mature upper surface; a blend of 149A and 150A, mature lower surface; a blend of 145A and 145B, fall color both surfaces; 145A, 178B, and 179B.

*Petioles*.—2.5 mm in length, 1 mm in width, strong, both surfaces matte and moderately pubescent with very short soft hairs 0.3 mm in length, too small to measure color, color; upper surface 151C, lower surface 151C to 151D.

*Stipules*.—None.

Inflorescence description:

*Inflorescence type*.—Compound cyme.

*Inflorescence size*.—Average of 3.1 cm in height and 3.8 cm in diameter.

*Peduncles*.—Average of 1 cm in length and 1 mm in diameter, strong, 146D in color, held in a vertical angle, surface is matte and densely covered with very short soft hairs, 0.2 mm in length, too small to measure color.

*Pedicels*.—Average of 4 mm in length and 0.8 mm in diameter, moderately strong, 146D in color, held in a 45° angle, surface is matte and densely covered with very short soft hairs; 0.2 mm in length, too small to measure color.

*Flower buds*.—Broadly elliptic to broadly ovate in shape, 2 mm in length, 1.5 mm in diameter, color; 178B, flushed with 182A, surface is matte and densely glandular, covered with glands that are 0.1 mm in length, color; 178B, flushed with 182A.

*Flower fragrance*.—None.

*Persistence of flowers*.—Self-cleaning.

*Flower quantity*.—Average of 140 per inflorescence, 1,000 per plant.

*Lastingness of inflorescence*.—An average of 10 days.

*Flower type*.—Rotate, single.

*Flower aspect*.—Upright to slightly outward.

*Flower size*.—Average of 9 mm in diameter and 6 mm in depth.

*Petals*.—5, average of 2.5 mm in length, 2 mm in width, broadly ovate in shape, obtuse apex, base is broadly cuneate and fused, margins entire and moderately to finely undulate, both surfaces smooth, matte, and glabrous, color: upper surface when opening; 70C, center 75B, lower surface when opening; 70C, center 75C, upper surface fully open; 73C, center 75B, lower surface fully open; 73C, center 75C.

*Calyx*.—Rotate, 1.5 mm in length, 3.5 mm in diameter.

*Sepals*.—5, rotate, alternating with the petals, 1.5 mm in length, 1 mm in width, deltoid in shape, acute apex, broadly cuneate base, fused, margins entire, surfaces are smooth and glabrous, upper surface moderately glossy, lower surface matte, color: upper surface when opening; 148B, lower surface when opening; 148A, upper surface when fully open; N148B, base 185D, lower surface when fully open; 148A, margins and base flushed with 185B.

Reproductive organs:

*Pistils*.—5, styles; 7 mm in length, 73B to 73C in color, stigmas; 1 mm in length, 0.3 mm in diameter, 73B to 73C in color, ovaries; superior, oblong in shape, 0.5 mm in length and 0.4 mm in width, 145B in color.

*Stamens*.—25, filaments; average of 4.5 mm in length, 73B to 73C in color, anthers; 0.3 mm in length, 0.31 mm in width, N77B in color, pollen; low in quantity, 155B in color.

*Fruit and seed*.—None observed to date.

It is claimed:

1. A new and distinct cultivar of *Spiraea* plant named 'Golden Jack' as herein illustrated and described.

* * * * *